(12) United States Patent
Deckers et al.

(10) Patent No.: US 6,183,762 B1
(45) Date of Patent: Feb. 6, 2001

(54) OIL BODY BASED PERSONAL CARE PRODUCTS

(75) Inventors: Harm M. Deckers; Gijs van Rooijen; Joseph Boothe; Janis Goll; Maurice M. Moloney, all of Calgary (CA)

(73) Assignee: Sembiosys Genetics Inc., Calgary (CA)

( * ) Notice: Under 35 U.S.C. 154(b), the term of this patent shall be extended for 0 days.

(21) Appl. No.: 09/448,600

(22) Filed: Nov. 24, 1999

Related U.S. Application Data

(63) Continuation-in-part of application No. 09/084,777, filed on May 27, 1998.
(60) Provisional application No. 60/047,753, filed on May 27, 1997, provisional application No. 60/047,779, filed on May 28, 1997, provisional application No. 60/075,863, filed on Feb. 25, 1998, and provisional application No. 60/075,864, filed on Feb. 25, 1998.

(51) Int. Cl.[7] ............... A61K 7/00; A23D 7/00; A23L 1/24; A23L 1/36; A23K 1/18
(52) U.S. Cl. ............ 424/401; 426/417; 426/601; 426/602; 426/605; 426/615; 426/629; 426/635; 426/805; 514/937; 516/53
(58) Field of Search ............... 424/401; 426/601, 426/602, 605, 615, 629, 635, 417, 805; 514/937; 516/53

(56) References Cited

U.S. PATENT DOCUMENTS

| | | | |
|---|---|---|---|
| 4,088,795 | * 5/1978 | Goodnight, Jr. et al. | 426/598 |
| 5,643,583 | * 7/1997 | Voultoury et al. | 424/401 |

* cited by examiner

*Primary Examiner*—Shelley A. Dodson
*Assistant Examiner*—Marina Lamm
(74) *Attorney, Agent, or Firm*—Bereskin & Parr

(57) ABSTRACT

The present invention provides novel emulsion formulations which comprise oil bodies. The invention also provides a method for preparing the emulsions and the use of the emulsions in various domestic and industrial compositions. The emulsions are especially suited for the preparation of food products, personal care products, pharmaceutical products and industrial products.

23 Claims, 2 Drawing Sheets

OIL BODY BASED PERSONAL CARE PRODUCTS

This application is a continuation-in-part of U.S. patent application Ser. No. 09/084,777 filed May 27, 1998 which claims benefit from U.S. provisional application No. 60/047,753, filed May 27, 1997; U.S. provisional application No. 60/047,779, filed on May 28, 1997; U.S. provisional application No. 60/075,863, filed on Feb. 25, 1998 and U.S. provisional application No. 60/075,864 filed on Feb. 25, 1998, all of which are incorporated herein by reference.

FIELD OF THE INVENTION

The present invention provides novel emulsions which comprise oil bodies. The invention also provides a method for preparing the emulsions and the use of the emulsions in various domestic and industrial compositions.

BACKGROUND OF THE INVENTION

Emulsions are mixtures which are prepared from two mutually insoluble components. It is possible to generate mixtures of homogenous macroscopic appearance from these components through proper selection and manipulation of mixing conditions. The most common type of emulsions are those in which an aqueous component and a lipophilic component are employed and which in the art are frequently referred to as oil-in-water and water-in-oil emulsions. In oil-in-water emulsions the lipophilic phase is dispersed in the aqueous phase, while in water-in-oil emulsions the aqueous phase is dispersed in the lipophilic phase. Commonly known domestic examples of emulsion-based formulations include mayonnaise, margarine, ice cream, cosmetics and paint. Emulsion systems are also extensively applied in industries such as the pharmaceutical and the agrochemical industries, where it is often desirable to formulate active ingredients in emulsions.

Generally emulsions are prepared in the presence of a multiplicity of other substances in order to achieve a desirable balance of emulsification, viscosity, stability and appearance. For example, the formulation of emulsions usually requires at least one, and frequently a combination of several, emulsifying agents. These agents facilitate the dispersal of one immiscable phase into the other and assist in stabilizing the emulsion. Emulsifiers comprise a wide variety of synthetic and natural components. For example, monoglycerides and chemical derivatives thereof, are widely used as emulsifiers in food applications such as margarines and baked products. An example of a natural emulsifier is lecithin, a phospholipid present in egg yolk, which is commonly used in the preparation of mayonnaise. It is also possible to entrap active ingredients in emulsions. This is especially desirable in compositions comprising active agents which are difficult to dissolve in aqueous solutions, such as certain vitamins and nucleotides. Active ingredients are also frequently formulated as emulsions in order to enhance their stability. One example of an emulsion system comprising a pharmaceutical agent is documented in U.S. Pat. No. 5,602,183 which discloses a wound healing composition containing an anti-inflammatory agent. The foregoing exemplifies only a few of the myriad of components which are included in formulations of emulsions known in the art. A comprehensive overview of emulsifying agents and their applications may be found in Becher, P. Encyclopedia of Emulsion Technology, Dekker Ed., 1983.

In the seeds of oilseed crops, which include economically important crops, such as soybean, rapeseed, sunflower and palm, the water insoluble oil fraction is stored in discrete subcellular structures variously known in the art as oil bodies, oleosomes, lipid bodies or spherosomes (Huang 1992, Ann. Rev. Plant Mol. Biol. 43: 177–200). Besides a mixture of oils (triacylglycerides), which chemically are defined as glycerol esters of fatty acids, oil bodies comprise phospholipids and a number of associated proteins, collectively termed oil body proteins. From a structural point of view, oil bodies are considered to be a triacylglyceride matrix encapsulated by a monolayer of phospholipids in which oil body proteins are embedded (Huang, 1992, Ann. Rev. Plant Mol. Biol. 43: 177–200). The seed oil present in the oil body fraction of plant species is a mixture of various triacylglycerides, of which the exact composition depends on the plant species from which the oil is derived. It has become possible through a combination of classical breeding and genetic engineering techniques, to manipulate the oil profile of seeds and expand on the naturally available repertoire of plant oil compositions. For an overview of the ongoing efforts in his area, see Designer Oil Crops/Breeding, Processing and Biotechnology, D. J. Murphy Ed., 1994, VCH Verlagsgesellschaft, Weinheim, Germany.

Plant seed oils are used in a variety of industrial applications, notably in the food, detergent and cosmetics industries. In order to obtain the plant oils used in these applications, seeds are crushed or pressed and subsequently refined using processes such as organic extraction, degumming, neutralization, bleaching and filtering. Aqueous extraction of plant oil seeds has also been documented (for example, Embong and Jelen, 1977, Can. Inst. Food Sci. Technol. J. 10: 239–243). Since the objective of the processes taught by the prior art is to obtain pure oil, oil bodies in the course of these production processes lose their structural integrity. Thus, the prior art emulsions formulated from plant oils do not generally comprise intact oil bodies.

Although there are many applications where mineral oil based products dominate the market, in other applications, oils derived from plant sources and fossil sources are in direct competition. Lauric oils, for example, which are widely used in the manufacture of detergents, are obtained from mineral oil as well as from coconut oil and more recently from genetically engineered rapeseed (Knauf, V. C., 1994, Fat. Sci. Techn. 96: 408). However, there is currently an increasing demand for biodegradable sources of raw materials. The plant oil body based emulsions of the present invention offer an advantage over similar mineral oil based formulations, in that the oil fraction is derived from a renewable and environmentally friendly source.

U.S. Pat. Nos. 5,683,740 and 5,613,583 disclose emulsions comprising lipid vesicles that have been prepared from crushed oleagenous plant seeds. In the course of the crushing process, oil bodies substantially lose their structural integrity. Accordingly, these patents disclose that in the crushing process, 70% to 90% of the seed oil is released in the form of free oil. Thus the emulsions which are the subject matter of these patents are prepared from crushed seeds from which a substantial amount of free oil has been released while the structural integrity of the oil bodies is substantially lost. In addition, the emulsions disclosed in both of these patents are prepared from relatively crude seed extracts and comprise numerous endogenous seed components including glycosylated and non-glycosylated non-oil body seed proteins. It is a disadvantage of the emulsions to which these patents relate that they comprise contaminating seed components imparting a variety of undesirable properties, which may include allergenicity and undesirable odour, flavour, colour and organoleptic characteristics, to the emulsions. Due to the presence of seed contaminants, the emulsions disclosed in these patents have limited applications.

SUMMARY OF THE INVENTION

The present invention relates to novel emulsion formulations which contain oil bodies. The emulsion formulations of the subject invention are obtainable in non-toxic and food grade forms. In addition, the emulsion formulations are advantageously prepared from an oil body preparation which is creamy in texture and thus may be readily applied in a variety of domestic and industrial applications. The present inventors have found that the oil body fraction of living cells is useful in the formulation of a variety of novel emulsion-based food, personal care, pharmaceutical and industrial products. Broadly stated, the present invention provides an emulsion formulation comprising washed oil bodies derived from a cell.

The invention also provides methods for preparing the emulsion formulations and the use of the emulsion formulations in various domestic and industrial compositions.

Accordingly, the present invention provides a method for preparing emulsion formulations comprising: 1) obtaining oil bodies from a cell; 2) washing the oil bodies; and 3) formulating the washed oil bodies into an emulsion.

In a preferred embodiment of the invention, the washed oil body preparation is obtained from plant seeds, including seeds obtainable from flax, safflower, rapeseed, soybean, maize and sunflower. Accordingly, the invention provides a method for preparing the emulsion formulations from plant seeds comprising:
   (a) grinding plant seeds to obtain ground seeds comprising substantially intact oil bodies;
   (b) removing solids from the ground seeds;
   (c) separating the oil body phase from the aqueous phase;
   (d) washing the oil body phase to yield a washed oil body preparation;
   (e) formulating the washed oil body preparation into an emulsion.

In a preferred embodiment of the invention, a liquid phase is added to the seeds prior to or while grinding the seeds.

In a further preferred embodiment of the invention, formulating the emulsion comprises adding a liquid phase to the washed oil body preparation.

The emulsions of the present invention can be used in a wide range of applications including in the preparation of food and feed products, pharmaceutical products, personal care products, and industrial products. The emulsion formulation of the present invention is especially suited for the preparation of food-grade products as it is non-toxic, creamy in texture and biodegradable.

Additional objects, advantages and features of the present invention will become apparent after consideration of the accompanying drawings and the following detailed description of the invention.

DETAILED DESCRIPTION OF THE INVENTION

Figure 1:
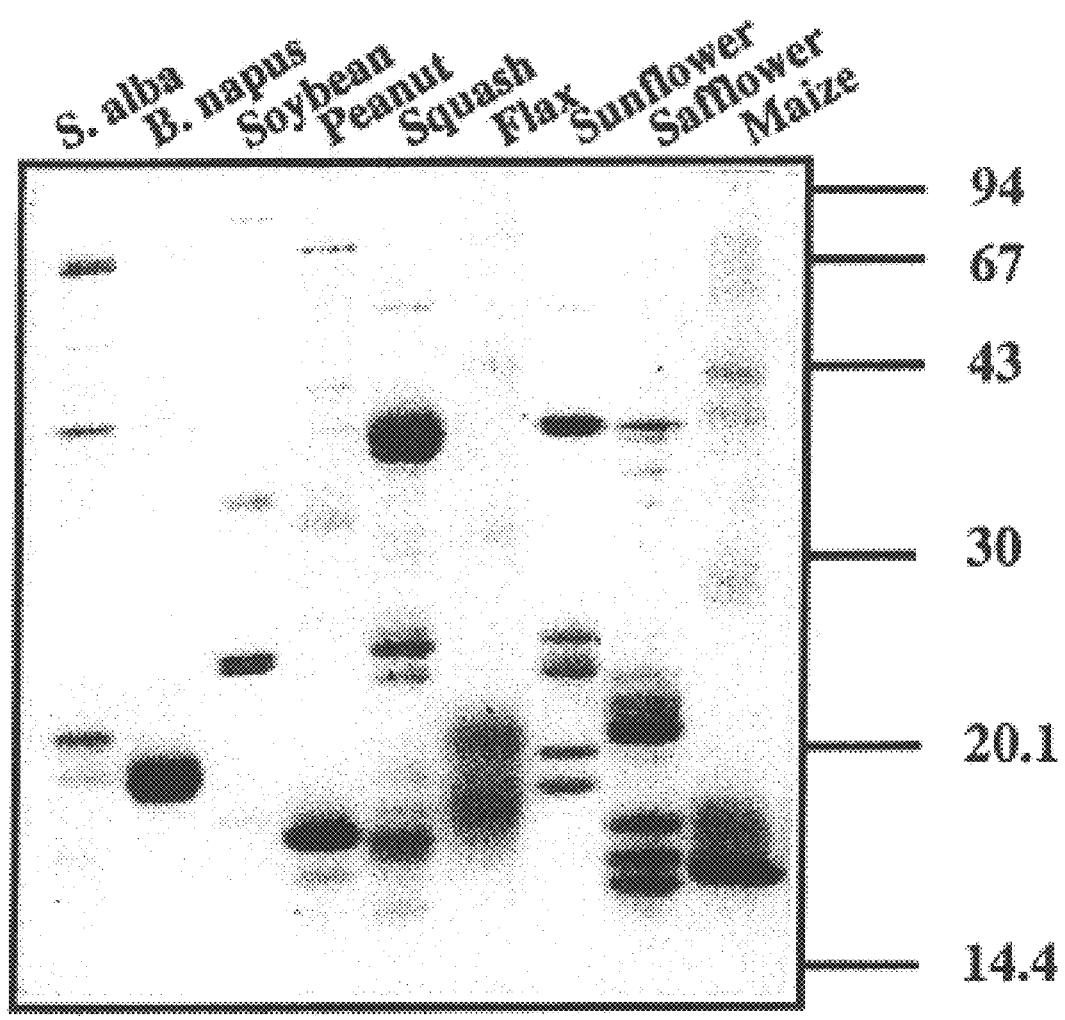
FIG. 1 is a Coomassie blue stained gel of a washed oil body preparation from white mustard, rapeseed (*Brassica napus*), soybean, peanut, squash, flax, sunflower, safflower and maize.

As hereinbefore mentioned, the present invention relates to emulsion formulations comprising oil bodies derived from a cell. In one embodiment, the present invention provides an emulsion formulation comprising washed oil bodies.

In another embodiment, the present invention provides a method for preparing an emulsion formulation comprising: 1) obtaining oil bodies from a cell; 2) washing the oil bodies; and 3) formulating the washed oil bodies into an emulsion.

The cell can be any cell that contains oil bodies (or oil-body like structures) including plant cells, animal cells, fungal cells and bacterial cells. In a preferred embodiment of the invention the oil bodies are obtained from a plant cell. The oil bodies may be obtained from a plant cell by rupturing the plant cell membrane and cell wall using any method which releases the cells constituents without substantially compromising the structural integrity of the oil bodies. More preferably, the oil bodies are obtained from plant seeds. Accordingly, the present invention further provides a method for preparing an emulsion formulation comprising:
   (1) obtaining oil bodies from plant seeds by a method that comprises:
      (a) grinding plant seeds to obtain ground seeds comprising substantially intact oil bodies;
      (b) removing solids from the ground seeds; and
      (c) separating the oil body phase from the aqueous phase;
   (2) washing the oil body phase to yield a washed oil body preparation; and
   (3) formulating the washed oil body preparation into an emulsion.

In a preferred embodiment of the invention, a liquid phase is added to the seeds prior to or while grinding the seeds.

In a further preferred embodiment of the invention, formulating the emulsion comprises adding a liquid phase to the washed oil body preparation.

The term "grinding" as used herein means milling, crushing, chopping or granulating the seeds and these terms may be used interchangeably throughout this application. In the process, the seed cells are broken open while the oil bodies remain substantially intact. The term "substantially intact" as used herein means that the oil bodies have not released greater than 50% (v/v) of their total seed oil content in the form of free oil. Preferably, grinding of the seeds results in release of less than about 50% (v/v) of the total seed oil content in the form of free oil, more preferably less than about 20% (v/v) and most preferably less than about 10% (v/v).

The term "solids" as used herein means any material that is not soluble in the aqueous phase or in the oil body phase, such as seed hulls.

The term "washing the oil bodies" as used herein means any process that removes cellular contaminants from the oil body phase, in particular any contaminant which imparts undesirable properties to the emulsion formulation, such as allergenic properties, undesirable colour, odour, flavour or organoleptic characteristics or any other undesirable property. Examples of methods of washing include gravitation based separation methods such as centrifugation and size exclusion based separation techniques such as membrane ultrafiltration and crossflow microfiltration. Washing methods and conditions are selected in accordance with the desired purity of the oil body preparation.

The term "washed oil body preparation" as used herein means a preparation of oil bodies from which a significant amount of cellular material has been removed including contaminants which impart undesirable properties to the emulsion formulation, such as allergenic properties, undesirable colour, odour, taste or organoleptic characteristics or any other undesirable property. Preferably, the washed oil body preparation contains less than about 75% (w/w) of all endogenously present non-oil body seed proteins, more preferably the washed oil body preparation contains less than about 50% (w/w) of endogenously present non-oil body seed proteins and most preferably less than about 10%(w/w) of endogenously present non-oil body seed proteins.

By "formulating the oil bodies into an emulsion", it is meant that the washed oil body preparation is mixed or homogenized, if necessary, until an emulsion is formed. In a preferred embodiment, an additional ingredient is added, such as a liquid phase, and the washed oil body preparation and the liquid phase are mixed until a homogenous mixture is attained.

The washed oil body preparations are particularly suitable for the formulation of emulsions due to advantageous properties outlined below.

Properties of the Oil Bodies

The emulsion formulations of the present invention comprise intact washed oil bodies of approximately uniform size, shape and density. When viewed under the electron microscope, oil bodies are found to be more or less spherically shaped structures (see: Example Murphy, D. J. and Cummins I., 1989, Phytochemistry, 28: 2063–2069; Jacks, T. J. et al., 1990, JAOCS, 67: 353–361). Typical sizes of oil bodies vary between 0.4 $\mu$m for and 1.5 $\mu$m (Murphy, D. J. and Cummins I., 1989, Phytochemistry, 28: 2063–2069). When analyzed using a Malvern Size Analyzer, it was found that oil bodies in a washed oil body preparation isolated from rapeseed were symmetrically and unimodally distributed around 1 $\mu$m. Using a Malvern Size Analyzer a washed oil body preparation could be clearly distinguished from commercially obtainable oil-in-water emulsions including soymilk, mayonnaise (Kraft Real Mayonnaise) and two coconut milk preparations (Tosca, Aroy-D). The exact size and density of the oil bodies depends at least in part on the precise protein/phospholipid/triacylglyceride composition which is present. Preparing washed oil bodies according to the present invention does not result in a substantive alteration in the shape of the oil bodies in comparison with those present in whole seed when viewed under the electron microscope.

Upon breaking open a cell containing oil bodies, the oil body fraction may be rapidly and simply separated from aqueous solutions since in aqueous solutions the oil body fraction will float upon application of centrifugal force. In solutions, where the density of the oil body fraction is greater than that of the solvent, such as 95% ethanol, the oil bodies will sediment under the same conditions. The oil body fraction may also be separated from the aqueous fraction through size-exclusion based separation techniques, such as membrane filtration, which may be advantageous in that more uniformly sized oil bodies may be acquired.

The oil bodies present in the washed oil body preparations of the present invention are resistant to exposure to strong acids and bases, including prolonged exposure to acidic conditions at least as low as pH 2 and alkaline conditions at least as high as pH 10. When exposed to pH 12, a slight loss of oil was observed, indicating a loss of integrity of the oil body structure. In addition, extraction with various organic solutions, including methanol, ethanol, hexane, isopropyl alcohol and ethyl acetate, does not or only slightly compromise the integrity of the oil bodies present in the washed oil body preparation. The oil bodies present in the washed oil body preparation were also found to withstand mixing with the anionic detergent, sodium dodecyl sulfate (SDS), the cationic, detergent hexadecyl trimethyl bromide and Tween-80, a non-ionic detergent. Boiling of the washed oil body preparation in the presence of SDS was found to result at least partly in disintegration of the oil body structure. The oil bodies present in the washed oil body preparation are stable when maintained for 2 hours up to at least 100° C. A slow freeze and thaw of washed oil body preparations resulted in a change in their physical appearance characterized by the formation of clumps as opposed to a homogeneous emulsion. Oil body clumping following a freeze-thaw could also be prevented to a large degree by either a) flash freezing in liquid nitrogen instead of slow freezing at −20° C. or b) adding glycerol in excess of 5% (v/v) to the oil body preparation prior to freezing. The resistance to relatively harsh chemical and physical conditions, is a unique characteristic of the oil bodies present in the washed oil body preparation of the subject invention.

The present invention provides emulsion formulations comprising oil bodies from which a significant amount of seed contaminants have been removed. These contaminants include proteins, volatiles and other compounds which may impart undesirable colour, odour, flavour, organoleptic characteristics or other undesirable characteristics. A number of seed proteins have been reported to cause allergenic reactions. For example, Ogawa et al. (1993, Biosci. Biotechnol. Biochem., 57:1030–1033) report allergenicity of the soybean glycoprotein P34 (alternatively referred to as Gly m Bd 30K). Allergenic reactions against rapeseed, wheat and barley seed proteins have also been reported (Armentia et al., 1993., Clin. Exp. Allergy 23: 410–415; Monsalve et al., 1993, Clin. Exp. Allergy 27: 833–841). Hence removal of contaminating seed proteins is advantageous. Washing conditions may be selected such that a substantially pure oil body preparation is obtained. In that case, only the oil body proteins are substantially present in the preparation.

For many applications, it is also considered desirable that a purer better defined oil body preparation is obtained, as this allows more control over the formulation process of the final emulsion. In order for the washed oil body preparation to be included in a diverse set of emulsions it is desirable that volatiles are kept to a minimum and the colour is preferably light or white. Washing of the oil body preparation results in a lighter coloured preparation. In addition, a substantial amount of volatiles is removed. Also removed by washing are compounds which promote the growth of microorganisms as it was observed that a washed oil body preparation had a longer shelf life than an unwashed preparation. Other compounds which are removed by washing include anti-nutritional glucosinilates and/or breakdown products thereof and fibrous material. When heat treated to 60° C. or 80° C., it was observed that larger quantities of water remained absorbed by the washed oil body preparation when compared with an unwashed preparation. Upon cooling down to room temperature and centrifugation, it was observed that the washed oil body preparation remained stable, while phase separation occurred in the unwashed preparation. Given the enhanced stability of washed oil bodies, they are preferred where the formulation process involves the application of heat. When heated to 40° C., the washed oil body preparation was able to absorb a larger quantity of exogenously added water without resulting in phase separation. Thus in the formulation of aqueous emulsions, washed oil bodies are preferred. The capacity to absorb exogenously added oils was also compared between a preparation of washed oil bodies and an unwashed preparation. Larger amounts of exogenous oil could be added to the washed oil body preparation before an unstable emulsion was formed. This is advantageous in formulations where exogenous oils or waxes are added in the formulation process such as where lubricants or personal care products are prepared. When viscosity was compared between a washed oil body preparation and an unwashed preparation it was found that the washed preparation was more viscous. A more viscous preparation of oil bodies is desirable as this eliminates the need for the addition of thickening agents in the formulation process.

Thus the washed oil body preparation provided here is superior to an unwashed preparation in many respects. The washed oil body preparation of the present invention is a better defined preparation with a longer shelf life and more preferable colour, odour and viscosity characteristics. The washed oil body preparation also has superior water and oil absorption characteristics. Finally due to the removal of a significant amount of seed proteins, allergenic reactions are less likely to occur. These characteristics allow the use of the washed oil body preparation in the formulation of a variety of domestic and industrial emulsions.

The above observations were made using washed and unwashed oil body preparations obtained from rapeseed and prepared as detailed in Example 2 of the present application. It is believed that resistance to relatively harsh chemical and physical conditions will be a characteristic of the oil bodies present in the washed oil preparation of the subject invention regardless of the source of the oil bodies. However one or more of the hereinbefore documented properties for rapeseed oil bodies may vary depending on the cells from which the washed oil bodies preparation is obtained. Nevertheless it is to be clearly understood that the subject invention is drawn to an oil body preparation which may be obtained from any cell comprising oil bodies.

In one embodiment of the present invention, the oil bodies are obtained from plant seeds. The presence of intact oil bodies in the emulsion and the described characteristics of these oil bodies clearly distinguish the subject emulsion formulation from other materials which may be prepared from plant seeds.

Sources and Preparation of the Oil Bodies

The washed oil body preparation of the subject may be obtained from any cell containing oil bodies or oil body-like organelles. This includes animal cells, plant cells, fungal cells, yeast cells (Leber, R. et al., 1994, Yeast 10: 1421–1428), bacterial cells (Pieper-Fürst et al., 1994, J. Bacterol. 176: 4328–4337) and algae cells (Rossler, P. G., 1988, J. Physiol. (London) 24: 394–400). In preferred embodiments of the invention the oil bodies are obtained from a plant cell which includes cells from pollens, spores, seed and vegetative plant organs in which oil bodies or oil body-like organelles are present (Huang, 1992, Ann. Rev. Plant Physiol. 43: 177–200). More preferably, the washed oil body preparation of the subject invention is obtained from a plant seed and most preferably from the group of plant species comprising: rapeseed (Brassica spp.), soybean (*Glycine max*), sunflower (*Helianthus annuus*), oil palm (*Elaeis guineeis*), cottonseed (Gossypium spp.), groundnut (*Arachis hypogaea*), coconut (*Cocus nucifera*), castor (*Ricinus communis*), safflower (*Carthamus tinctorius*), mustard (Brassica spp. and *Sinapis alba*), coriander (*Coriandrum sativum*), squash (*Cucurbita maxima*), linseed/flax (*Linum usitatissimum*), Brazil nut (*Bertholletia excelsa*). jojoba (*Simmondsia chinensis*) and maize (*Zea mays*). Plants are grown and allowed to set seed using agricultural cultivation practises well known to a person skilled in the art. After harvesting the seed and if desired removal of material such as stones or seed hulls (dehulling), by for example sieving or rinsing, and optionally drying of the seed, the seeds are subsequently processed by mechanical pressing, grinding or crushing. In a preferred embodiment, a liquid phase is added prior to or while grinding the seeds. This is known as wet milling. Preferably the liquid is water although organic solvents such as ethanol may also be used. Wet milling in oil extraction processes has been reported for seeds from a variety of plant species including: mustard (Aguilar et al 1990, Journal of Texture studies 22:59–84), soybean (U.S. Pat. No. 3,971,856; Carter et al., 1974, J. Am. Oil Chem. Soc. 51:137–141), peanut (U.S. Pat. Nos. 4,025,658; 4,362,759), cottonseed (Lawhon et al., 1977, J. Am. Oil, Chem. Soc. 63:533–534) and coconut (Kumar et al., 1995, INFORM 6 (11):1217–1240). It may also be advantageous to imbibe the seeds for a time period from about fifteen minutes to about two days in a liquid phase prior grinding. Imbibing may soften the cell walls and facilitate the grinding process. Imbibition for longer time periods may mimic the germination process and result in certain advantageous alterations in the composition of the seed constituents. Preferably the added liquid phase is water.

The seeds are preferably ground using a colloid mill, such as the MZ130 (Fryma Inc.). Besides colloid mills, other milling and grinding equipment capable of processing industrial scale quantities of seed may also be employed in the here described invention including: flaking rolls, disk mills, colloid mills, pin mills, orbital mills, IKA mills and industrial scale homogenizers. The selection of the mill may depend on the seed throughput requirements as well as on the source of the seed which is employed. It is of critical importance that seed oil bodies remain substantially intact during the grinding process. Grinding of the seeds therefore results in the release of preferably less than about 50% (v/v) of the total seed oil content in the form of free oil, more preferably less than about 20% (v/v) and most preferably less than about 10% (w/w). Any operating conditions commonly employed in oil seed processing, which tend to disrupt oil bodies are unsuitable for use in the process of the subject invention. Milling temperatures are preferably between 10° C. and 90° C. and more preferably between 26° C. and 30° C., while the pH is preferably maintained between 2.0 and 10.

Solid contaminants, such as seed hulls, fibrous material, undissolved carbohydrates and proteins and other insoluble contaminants, are removed from the crushed seed fraction. Separation of solid contaminants, may be accomplished using a decantation centrifuge, such as a HASCO 200 2-phase decantation centrifuge or a NX310B (Alpha Laval). Depending on the seed throughput requirements, the capacity of the decantation centrifuge may be varied by using other models of decantation centrifuges, such as 3-phase decanters. Operating conditions vary depending on the particular centrifuge which is employed and must be adjusted so that insoluble contaminating materials sediment and remain sedimented upon decantation. A partial separation of the oil body phase and liquid phase may be observed under these conditions.

Following the removal of insoluble contaminants, the oil body phase is separated from the aqueous phase. In a preferred embodiment of the invention a tubular bowl centrifuge is employed. In other embodiments, hydrocyclones, disc stack centrifuges, or settling of phases under natural gravitation or any other gravity based separation method may be employed. It is also possible to separate the oil body fraction from the aqueous phase employing size exclusion methods, such as membrane ultrafiltration and crossflow microfiltration. In preferred embodiments the tubular bowl centrifuge is a Sharples model AS-16 (Alpha Laval) or a AS-46 Sharples (Alpha Laval). A critical parameter is the size of the ring dam used to operate the centrifuge. Ring dams are removable rings with a central circular opening varying, in the case of the AS-16, from 28 to 36 mm and regulate the separation of the aqueous phase from the oil body phase thus governing the purity of the oil body fraction which is obtained. In preferred embodiments, a ring dam size of 29 or 30 mm is employed when using the AS-16. The exact ring dam size employed depends on the type of oil seed which is used as well as on the desired final consistency of the oil body preparation. The efficiency of separation is further affected by the flow rate. Where the AS-16 is used flow rates are typically between 750–1000 ml/min (ring dam size 29) or between 400–600 ml/min (ring dam size 30) and temperatures are preferably maintained between 26° C. and 30° C. Depending on the model centrifuge used, flow rates and ring dam sizes must be adjusted so that an optimal separation of the oil body fraction from the aqueous phase is achieved. These adjustments will be readily apparent to a skilled artisan.

Separation of solids and separation of the aqueous phase from the oil body fraction may also be carried out concomitantly using a gravity based separation method such as 3-phase tubular bowl centrifuge or a decanter or a hydrocyclone or a size exclusion based separation method.

The compositions obtained at this stage in the process, generally are relatively crude and comprise numerous endogenous seed proteins, which includes glycosylated and non-glycosylated proteins and other contaminants such as starch or glucosinilates or breakdown products thereof. The present invention comprises the removal of a significant amount of seed contaminants. To accomplish removal of contaminating seed material, the oil body preparation obtained upon separation from the aqueous phase is washed at least once by resuspending the oil body fraction and centrifuging the resuspended fraction. This process yields what for the purpose of this application is referred to as a washed oil body preparation. The number of washes will generally depend on the desired purity of the oil body fraction. Depending on the washing conditions which are employed, an essentially pure oil body preparation may be obtained. In such a preparation the only proteins present would be oil body proteins. In order to wash the oil body fraction, tubular bowl centrifuges or other centrifuges such hydrocyclones or disc stack centrifuges may be used. Washing of oil bodies may be performed using water, buffer systems, for example, sodium chloride in concentrations between 0.01 M and at least 2 M, 0.1 M sodium carbonate at high pH (11–12), low salt buffer, such as 50 mM Tris-HCl pH 7.5, organic solvents, detergents or any other liquid phase. In preferred embodiments the washes are performed at high pH (11–12). The liquid phase used for washing as well as the washing conditions, such as the pH and temperature, may be varied depending on the type of seed which is used. Washing at a number of different pH's between pH 2 and pH 11–12 may be beneficial as this will allow the step-wise removal of contaminants, in particular proteins. Preferably washing conditions are selected such that the washed oil body preparation comprises less than about 75%(w/w) of all endogenously present non-oil body seed proteins, more preferably less than about 50% (w/w) of endogenously present non-oil body seed proteins and most preferably less than about 10% (w/w) of endogenously present non-oil body proteins. Washing conditions are selected such that the washing step results in the removal of a significant amount of contaminants without compromising the structural integrity of the oil bodies. In embodiments where more than one washing step is carried out, washing conditions may vary for different washing steps. SDS gel electrophoresis or other analytical techniques may conveniently be used to monitor the removal of endogenous seed proteins and other contaminants upon washing of the oil bodies. It is not necessary to remove all of the aqueous phase between washing steps and the final washed oil body preparation may be suspended in water, a buffer system, for example, 50 mM Tris-HCl pH 7.5, or any other liquid phase and if so desired the pH may be adjusted to any pH between pH 2 and pH 10.

The process to manufacture the washed oil body preparation may be performed in batch operations or in a continuous flow process. Particularly when tubular bowl centrifuges are used, a system of pumps operating between steps (a) and (b), (b) and (c), and (c) and (d) a continuous flow throughout the processing system is generated. In a preferred embodiment, the pumps are 1 inch M2 Wilden air operated double diaphragm pumps. In other embodiments, pumps, such as hydraulic or peristaltic pumps may be employed. In order to maintain a supply of homogenous consistency to the decantation centrifuge and to the tubular bowl centrifuge, homogenizers, such as an IKA homogenizer may be added between the separation steps. In-line homogenizers may also be added in between various centrifuges or size exclusion based separation equipment employed to wash the oil body preparations. Ring dam sizes, buffer compositions, temperature and pH may differ in each washing step from the ring dam size employed in the first separation step.

In embodiments of the invention where the oil bodies are isolated from softer tissues, for example the mesocarp tissue of olives, the techniques applied to break open the cell may vary somewhat from those used to break harder seeds. For example, pressure-based techniques may be preferred over crushing techniques. The methodology to isolate oil bodies on a small scale has been reported for isolation of oil bodies from mesocarp tissues in olive (*Olea europaea*) and avocado (*Persea americana*) (Ross et al., Plant Science, 1993, 93: 203–210) and from microspore-derived embryos of rapeseed (*Brassica napus*) (Holbrook et al., Plant Physiol., 1991, 97: 1051–1058).

In embodiments of the invention where oil bodies are obtained from non-plant cells, the washed oil body preparation is isolated following similar procedures as outlined above. The methodology to isolate oil bodies from yeast has been documented (Ting et al., 1997, Journal Biol. Chem. 272:3699–3706).

The chemical and physical properties of the oil fraction may be varied in at least two ways. Firstly, different plant species contain oil bodies with different oil compositions. For example, coconut is rich in lauric oils ($C_{12}$), while erucic acid oils ($C_{22}$) are abundantly present in some Brassica spp. Secondly, the relative amounts of oils may be modified within a particular plant species by applying breeding and genetic engineering techniques known to the skilled artisan. Both of these techniques aim at altering the relative activities of enzymes controlling the metabolic pathways involved in oil synthesis. Through the application of these techniques, seeds with a sophisticated set of different oils are obtainable. For example, breeding efforts have resulted in the development of a rapeseed with a low erucic acid content (Canola) (Bestor, T. H., 1994, Dev. Genet. 15: 458) and plant lines with oils with alterations in the position and number of double bonds, variation in fatty acid chain length and the introduction of desirable functional groups have been generated through genetic engineering (Töpfer et al., 1995, Science, 268: 681–685). Using similar approaches a person skilled in the art will be able to further expand on the presently available sources of oil bodies. Variant oil compositions will result in variant physical and chemical properties of the oil bodies. Thus by selecting oilseeds or mixtures thereof from different species or plant lines as a source for oil bodies, a broad repertoire of emulsions with different textures and viscosities may be acquired.

Formulating the Emulsion

The washed oil body preparation may be formulated into an emulsion using techniques known in the art. Preferably, at least one additional ingredient is added to the washed oil body preparation. The additional ingredient may be added as a solution, suspension, a gel or solid and quantities of the additional ingredient will depend on the formulation. The additional ingredient may upon formulation become associated with the oil bodies for example by the formation of non-covalent bonds with the oil body, remain suspended in solution, or form a suspension in which the oil bodies are dispersed. The ingredient may also penetrate the phospholipid monolayer surrounding the oil body or the triacylglyceride matrix. Ingredients which may penetrate the oil body include oils, waxes and the colorant Nile Red. In a preferred embodiment, the additional ingredient is a liquid phase. In a further preferred embodiment the liquid phase is water. Water may be added either directly or through moisture associated with another ingredient. The final amount of water is not critical, as long as upon mixing of the ingredients, a stable emulsion is formed. Generally, the compositions will contain at least 1% of water and up to 99% water. Usually mixing will be required to provide an adequate emulsion and it may be necessary to apply heat or pressure.

In another preferred embodiment the additional ingredient is an oil or a wax. Oils or waxes may partition to the triacyl glyceride matrix of the oil bodies and in this manner lipid soluble ingredients, such as lipid soluble vitamins may be delivered to the oil body matrix. Where oils or waxes comprise the added ingredient, the oil bodies may remain suspended in the lipophilic phase or double emulsions may be formed.

The final compositions may be in solid or in liquid form or of any other desired viscosity. The viscosity of the emulsion may be modified using a viscosity modifier such as cetyl alcohol. The emulsion may be thickened using gelling agents such as cellulose and derivatives, Carbopol and derivatives, carob, carregeenans and derivatives, xanthane gum, sclerane gum, long chain alkanolamides, bentone and derivatives, Kaolin USP, Veegum Ultra, Green Clay, Bentonite NFBC, typically present in concentrations less than 2% by weight.

The emulsion may further comprise surfactants to wet, foam, penetrate, emulsify, solubilize, stabilize and or disperse a selected material. For example anionic surfactants such as sodium coconut monoglyceride sulphonate, cationic surfactants, such as lauryl trimethyl ammonium chloride, cetyl pyridinium chloride and trimethylammonium bromide, nonionic surfactants including pluronics, and polyethylene oxide condensates of alkyl phenols, and zwitterionic surfactants such as derivatives of aliphatic quaternary ammonium, phosmomium and sulphonium compounds may all be added as required.

Chelating agents, capable of binding metal ions, such as tartaric acid, EDTA, citric acid, alkali metal citrates, pyrophosphate salts or anionic polymeric polycarboxylates may be also included in the emulsion formulation as desired.

Generally, the emulsion formulations will be treated such that contamination by bacteria, fungi, mycoplasmas, viruses and the like or undesired chemical reactions, such as oxidative reactions are prevented thus allowing the preparation of a stable final product with a shelf-life accepetable for the final formulation. In preferred embodiments this is accomplished by the addition of preservatives, for example sodium metabisulfite, Glydant Plus, Phenonip, methylparaben propylparaben, Germall 115, Germaben II, phytic acid, or other chemical additives, by irradiation, for example by ionizing radiation such as cobalt-60 or cesium-137 irradiation or by ultraviolet irradiation or by heat treatment for example by pasteurization in a constant temperature water bath at approximately 65° C. for 20 minutes. The pasteurization temperature preferably ranges between 50° C. and 90° C. and the time for pasteurization preferably ranges between 15 seconds to 35 minutes. Oxidative reactions may be prevented by the addition of anti-oxidants such as butylated hydroxytoluene (BHT) or butylated hydroxyanisol (BHA) or other anti-oxidants.

The physical stability of the formulation may be further enhanced if desired by the addition of an emulsifier such as for example Arlacel. Typically, emulsion stabilizers are added in small amounts (less than 2% (w/w).

In addition, active agents may be added to the washed oil body preparation. For example personal care compositions may be formulated as stable suspensions using the present emulsion formulation and vitamins and moisturizing agents may be included in skin creams. One particularly advantageous way in which an active ingredient may be included in emulsions of the subject invention, is through construction of oleosin gene fusions as detailed in WO 96/21029. Briefly stated, WO 96/21029 discloses a method of producing proteins and peptides as fusion proteins of oleosins. These fusion proteins are created by genetically linking the gene encoding oleosin to a gene encoding a peptide or protein of interest. Expression of the fusion gene, in for example an oilseed plant, results in synthesis of a fusion protein which is then targeted to the oil body. Isolation of the oil body fraction results in recovery of the fusion protein. In principle any desired protein or peptide may be produced using this technology. For example, it is envisaged that polar fish antifreeze peptides (Davies, P. L. et al. 1990, FASEB J. 4: 2460–2468) are produced as oleosin fusion proteins. The washed oil body preparation may then be employed to prepare ice creams, milkshakes or other frozen foodgrade materials with improved freezing properties by inhibiting or preventing ice crystal formation. In another example, a therapeutic protein may be produced as an oleosin fusion. The oil bodies may then be used to formulate a desirable suspension which may be for oral consumption, or for topical skin application. This embodiment of the present invention is further exemplified in example 11 of the present invention where a fish food is prepared which comprises oil bodies comprising an oleosin—carp growth hormone fusion.

An emulsion with film forming properties may also be formulated. Such an emulsion when it is applied to a surface and dried forms a coating. An example of an emulsion where a coated oil body film is applied is in fish food, where oil bodies may be applied to the fish food to enhance the dietary value. A film forming emulsion is particularly useful in embodiments of the present invention where controlled release of an active ingredient is desirable such as in delivery of pharmaceuticals or volatiles such as fragrances. The release time of the active agent from a film of emulsion, which occurs during drying, depends, among other factors, on the thickness of the film. When a thicker coating is applied a longer drying time will result in a slower release of the active agent. In variant contemplated formulations, release of the agent occurs only when the film is dry. Other factors, such as the composition of the emulsion and the type and concentration of the active ingredient also determine the characteristics of release. For example, cosolvents, such as ethanol, may be included in the formulation and influence the release time. Release of an active ingredient is also desirable in food applications, where a flavorant entrapped in an emulsion is released during consumption. The release of the flavorant, depending on the exact formulation of the emulsion, may elicit a sudden intense sensation or a more subtle blend of flavours and essences.

The emulsion formulation may also be used in sprays and aerosols. Preferably small sized oil bodies, for example 1 $\mu$m or less in diameter such as those found in *B. napus,* are used for this purpose. Volatiles, such as alcohol and fragrances may be included in these sprays. Emulsions of this type may also be sprayed onto the surface of dried food preparations such as potato chips and dried soup. The emulsion might include a flavorant and add preservative value or assist in maintaining the appropriate moisture levels of the food.

Uses of the Emulsion Formulation

The subject invention is directed toward the production of emulsions that are useful in industrial and domestic compositions. It is noted that the emulsions may be applied in compositions which vary widely in physical properties and use. Thus specific embodiments include applications such as food and feed products, pharmaceutical products, personal care products and industrial products.

Food and feed uses include non-dairy substitutes, such as non-dairy cheese or yoghurt, margarines, mayonnaises, vinaigrettes, icings, ice creams, salad dressings, synthetic mustards, candy, chewing gum, pudding, baking products, condiments, juice clouding agents, baby formula, flavour carriers, texturing agents (shortening), pet food, fish food and livestock feed. Personal care products applications include soaps, cosmetics, skin creams, facial creams, night cream, day cream, a face mask, skin cleanser, tooth paste, lipstick, perfumes, make-up, foundation, blusher, mascara, eyeshadow, sunscreen lotions, hair conditioner, and hair colouring. Pharmaceutical products which may be formulated using the washed oil body preparation of the subject invention include therapeutic agents, diagnostic agents and delivery agents. As a therapeutic or diagnostic agent, the emulsion will additionally contain an active ingredient. The active ingredient can be anything that one wishes to deliver to a host. In one embodiment, the active ingredient may be a protein or peptide that has therapeutic or diagnostic value. Such peptides include antigens (for vaccine formulations), antibodies, cytokines, blood clotting factors and growth hormones. Industrial uses for the emulsions of the present invention include paints, coatings, lubricants, films, gels, drilling fluids, paper sizing, latex, building and road construction material, inks, dyes, waxes, polishes and agrochemical formulations. In preferred embodiments, the subject invention is directed to compositions which may be ingested by animals and humans. Since, these compositions may be ingested they must be of foodgrade quality. The particular product and the particular form in which the emulsion is applied, however is not of critical importance and may be as desired. It is to be clearly understood that the emulsion formulated with the washed oil body preparation may be applied in any domestic or industrial product.

The stability of the present emulsion formulation at low pH may be exploited in formulations of acid emulsions. For example, the emulsion formulation may be used in the preparation of a mayonnaise-like foodproduct, which besides the washed oil body preparation comprises a vegetable oil, mustard, vinegar and egg yolk, if desired. Pourable emulsions, such as salad dressings may be prepared by increasing the relative amount of vinegar and/or by the addition of water.

An example of an application where heat may be applied without apparent deleterious effects, is in the preparation of a savory sauce such as a bechamel sauce or in sweet sauces such as chocolate sauces. In these applications, the washed oil body preparation is employed as a frying substitute. To prepare a bechamel sauce, to 1 part of the heated washed oil body preparation, 1 part (w/w) of flour is added and stirred until a thick suspension is formed. At moderate heat milk is gradually added until a sauce with a desired viscosity is obtained.

The emulsion formulation may also be used as a butter substitute. In this application, small amounts of water are added to the washed oil body preparation, for example, less than 10% until a desired viscosity is obtained. Natural butter flavours and thickeners may be added as desired. The butter substitute may be used on sweet corn, bread, in cake mixes or bread making. Salt, which contributes flavour and acts as a preservative may be added typically to a level of about 2.5% (wt/vol). Colour agents, for example, extracts of annatto seed or carotene may be added to deepen the colour as desired. An advantage of this application is that the oil body based butter does not comprise hydrogenated fatty acids, which are used in the formulations of margarines and the like to achieve a desirable consistency, but are also with associated with cardiovascular diseases.

Shortenings may be prepared to various degrees of stiffness, from a foam to a pourable shortening. In this application, air is beaten into the emulsion formulation and the emulsion formulation can be considered to be dispersed into the continuous phase, air. Shortenings may be applied to mixes where creaming and fluffing are desired. These mixes include icings, synthetic creams, ice creams and cake batter.

An imitation fruit juice may be prepared from artificial or natural flavours and nutrients. Such imitation juices do not have the correct appearance and due to transparency appear to be weak or diluted. By adding a small amount, for example 0.1 to 1% (v/v) of the washed oil body preparation or an emulsion thereof clouding may occur to give the juice a rich appearance. Thus the present oil body preparation may be used as a clouding agent.

In another application involving juices, the washed oil body preparation or an emulsion thereof may be added to juices with settleable solids, such as tomato juice. Adding a small amount of the washed oil body preparation, for example 0.1 to 1% (v/v), may decrease the rate of settling of the solids in the juice and assist in maintaining the rich appearance.

The washed oil body preparation of the present invention may also be used to prepare personal care products including cosmetic and cosmeceutical products. In this embodiment the emulsion is formulated as a dermatologically acceptable emulsion, which may for example be employed to apply facially and/or to the body skin, including nails, teeth and lips. The formulation may have properties to combat ageing of the skin, acne, pigmentation, hair loss, or promote hair removal or facilitate wound healing and/or restructuring of the skin tissue. The washed oil body preparation represents preferably 1–99% by weight of the final composition. In order to formulate a personal care product it may be advantageous to first formulate a base formulation comprising oil bodies. The base formulation may subsequently be used to formulate the final personal care product (See Examples 12–21).

The pesonal care compositions of the present invention may comprise additional hydrocarbon compounds such as plant, animal, mineral or synthetic oils or waxes or mixes thereof. They comprise paraffin, petrolatum, perhydrosqualene, arara oil, almond oil, calphyllum oil, avocado oil, sesame oil, castor oil, jojoba oil, olive oil, or cereal germ oil. Esters may be included such as esters of lanolic acid, oleic acid, lauric acid, stearic acid, myristic acid. It is also possible to include alcohols for example, oleoyl alcohol, linoleyl alcohol or linolenyl alcohol, isostearyl alcohol or octyl dodecanol, alcohol or polyalcohol. Further hydrocarbons which may be included are octanoates, decanoates, ricinoleates, caprylic/capric triglycerides or $C_{10}$ to $C_{22}$ fatty acid triglycerides. Addition of these agents may result in the formation of double emulsions.

Hydrogenated oils, which are solid at 25° C., such as hydrogenated castor oil, palm oil or coconut oil, or hydrogenated tallow; mono- di- tri- or sucroglycerides; lanolins; and fatty acids which are solid at 25° C. may also be included in the personal care formulations of the present invention. Among the waxes which may be included are animal waxes such as beeswax; plant waxes such as carnauba wax, candelilla wax, ouricurry wax, Japan wax or waxes from cork fibres or sugar cane; mineral waxes, for example paraffin wax, lignite wax, microcrystalline waxes or ozokerites and synthetic waxes.

Pigments may be included and may be white or coloured, inorganic or organic and/or paerlescent. These pigments comprise titanium dioxide, zinc oxide, ziriconium dioxide, black, yellow, red and brown iron oxides, cerium dioxide, chromium oxide, ferric blue, carbon black, barium, strontium, calcium and aluminum lakes and mica coated with titanium oxide or with bismuth oxide.

Active ingredients commonly employed in skin creams, such as vitamins, for example as vitamin A or C, E and alpha hydroxy acids, such as citric, glycolic, lactic, gammalinolenic and tartaric, into cosmetic and/or dermatological compositions may be included. For example, U.S. Pat. No. 5,602,183 teaches that vitamin C or ascorbic acid promotes growth of connective tissue, particularly in the skin strengthens the skin against external aggressions such as from smoke and UV radiation. Moisturizing agents which may be included in personal care products such as skin creams are for example glycerine, panthenol, mineral oil and urea. Antioxidants such as the naturally occurring tocopherols and polyphenols, or butylated hydroxytoluene (BHT) and hydroxyanisole (BHA), retinyl palmitate and vitamin E acetate may also be also added. Emolients, such as Finsolv TN, Sesame oil, isohexadecane, safflower oil, permethyl 101 A, Trivent OC-G, may be added if desired. Soothing agents which may be added include for example Allantoin. Skin protectants which may be used to formulate the oil body based personal care products of the present invention include dimethicone and SEE 839. A penetrating agent such as Trivalin SF and an exfolient for example Palemol OL or glycolic acid may also be added. Sunscreens such as octyl methoxycinnamate (Parsol MCX), 3-benzophenone (Uvinul M40) and butylmethoxydibenzoylmethane (Parsol 1789) may be employed to prepare a sun tanning lotion. Pharmaceutically active ingredients which may be used to formulate cosmetic compositions include for example antibiotics, fungicides and anti-inflammatory agents.

The final personal care product may be in the form of a free, poured or compacted powder (foundation, blusher or eyeshadow), a relatively greasy product such as lipstick, mascara, or an oil or lotion for the body or face.

The washed oil body preparation may also be used to serve as an orally acceptable carrier in toothpaste which may further comprise silicas, surfactants, chelating agents, a fluoride, thickeners, sweeteners, flavorants, for example as oil of peppermint, enzymes and biocides.

An example of an industrial product which may be formulated is paint wherein the main resin, such as those based on silicone type compounds, acrylic compounds, polyester, akyd, fluorine, epoxy, polyurethane may be partly or entirely replaced by the washed oil body preparation of the present invention. Further additives such as pigments, dyes, glass flakes, and aluminum flakes, pigment dispersants, thickeners, levelling agents, hardening catalysts, hardening agents such as dioisocyanates, hardening catalysts, gelling inhibitors, ultraviolet absorbing agents, free radical quenching agents etc. may be formulated in paint compositions as required.

The washed oil body preparation may also be to formulate lubricants. For example, the washed oil body preparation may be used to partially or entirely replace the lubricating oils such as animal oils, vegetable oils, petroleum lubricating oils, synthetic lubricating oils, or the lubricating grease such as lithium grease, urea grease and calcium grease. Other compositions employed in a lubricant formulation comprise antioxidants, detergent dispersants, oilness agents, friction modifiers, viscosity index improvers, pour point depressants, solid lubricant material, rust inhibitors and antifoamers.

Waxes may also be prepared using the washed oil body preparation of the present invention. These comprise rinsewax types, such as those providing a stable hydrophobic film-finish onto automobiles and other protective coatings. Other compositions used in the preparation of a wax comprise surfactants, mineral oils, such as mixed paraffinic and aromatic/naphtenic oils, perfumes, biocides, colouring agents which may be added in compatible amounts as desired.

Where industrial products, such as paints or lubricants are formulated, purity of the oil body phase may be less critical and it may not be necessary to subject the oil bodies to washing. An industrial emulsion may be prepared by (i) obtaining oil bodies from a cell and (ii) formulating the oil bodies into an industrial emulsion. The oil bodies may be obtained by (a) grinding plant seeds; (b) removing solids from the ground seeds; and (c) separating the oil body phase from the aqueous phase. The invention also includes an industrial emulsion comprising oil bodies prepared according to the present invention.

The following non-limiting examples are illustrative of the present invention:

EXAMPLES

Example 1

Obtaining a washed oil body preparation from oilseed rape, soybean, sunflower, white mustard, peanut, squash, flax, safflower and maize—laboratory scale. Dry mature seeds obtained from *Brassica napus* cv Westar, soybean, sunflower, white mustard, peanut, squash, flax, safflower and maize were homogenized in five volumes of cold grinding buffer (50 mM Tris-HCl, pH 7.5, 0.4 M sucrose and 0.5 M NaCl) using a polytron operating at high speed. The homogenate was centrifuged at 10×g for 30 minutes in order to remove particulate matter and to separate oil bodies from the aqueous phase containing the bulk of the soluble seed protein. The oil body fraction was skimmed from the surface of the supernatant with a metal spatula and added to one volume of grinding buffer. In order to achieve efficient washing in subsequent steps it was found to be necessary to thoroughly redisperse the oil bodies in the grinding buffer. This was accomplished by gently homogenizing the oil bodies in grinding buffer using a polytron at low speed. Using a syringe, the redispersed oil bodies were carefully layered underneath five volumes of cold 50 mM Tris-HCl pH 7.5 and centrifuged as above. Following centrifugation, the oil bodies were removed and the washing procedure was repeated two times. The final washed oil body preparation was resuspended in one volume of cold Tris-HCl pH 7.5, redispersed with the polytron.

The oil body samples were dissolved in SDS sample buffer and then analyzed by SDS gel electrophoresis. The results are shown in FIG. 1.

The material thus obtained material was then ready to be employed in various formulations.

Example 2

Obtaining a washed oil body preparation from oilseed rape, sunflower and maize on a large scale. This example describes the recovery of the oil body fraction from canola, sunflower and maize seed on a large scale. The resulting preparation contains intact oil bodies and is comparable in purity with a preparation obtained using laboratory scale procedures.

Grinding of seeds. A total of 10–15 kgs of dry canola seed (*Brassica napus* cv Westar), sunflower (*Helianthus annuus*) or maize (*Zea mays*) was poured through the hopper of a colloid mill (Colloid Mill, MZ-130 (Fryma); capacity: 500 kg/hr), which was equipped with a MZ-120 crosswise toothed rotor/stator grinding set and top loading hopper. Approximately 50–75 l water was supplied through an externally connected hose prior to milling. Operation of the mill was at a gap setting of 1R, chosen to achieve a particle size less than 100 micron at 18° C. and 30° C. Following grinding of the seeds tap water was added to the seed slurry to a final volume of 90 liters.

Removal of solids. The resulting slurry, was pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge at a flow rate of 360 L/hr was achieved using a 1 inch M2 Wilden air operated double diaphragm pump. In 15–20 minutes approximately 15 kg of seed was decanted.

Oil body separation. Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 30 mm. Operating speed was at 15,000 rpm (13,200×g). A Watson-Marlow (Model 704) peristaltic pump was used to pump the decanted liquid phase (DL) into the tubular bowl centrifuge after bringing the centrifuge up to operating speed. This results in separation of the decanted liquid phase into a heavy phase (HP) comprising water and soluble seed proteins and a light phase (LP) comprising oil bodies. The oil body fraction which was obtained after one pass through the centrifuge is referred to as an unwashed oil body preparation. The oil body fraction was then passed through the centrifuge three more times. Between each pass through the centrifuge, concentrated oil bodies were mixed with approximately five volumes of fresh water. The entire procedure was carried out at room temperature. The preparations obtained following the second separation are all referred to as the washed oil body preparation. Following three washes much of the contaminating soluble protein was removed and the oil body protein profiles obtained upon SDS gel electrophoresis were similar in appearance to those obtained using laboratory scale procedures.

The large scale oil body preparation may be pasteurized. Pasteurization is achieved by initially thickening the washed oil bodies with centrifugation to a water content of 30 to 60%, preferable between 35 and 50% weight and most preferable between 37 and 40% weight. The thickened oil body solution can then be pasteurized in a constant temperature water bath at approximately 65° C. for 20 minutes. The pasteurization temperature could range between 50 and 90° C. and the time for pasteurization could range between 15 seconds to 35 minutes. If the oil bodies are used in a cosmetic formulation, then before pasteurization, 0.1% Glydant Plus, 0.1% BHA and 0.1% BHT may be added as a preservative and anti-oxidants respectively.

Example 3

Removal of seed proteins by washing the oil body phase. This example describes the recovery of a washed oil body fraction from canola, maize and sunflower seed. Using different washing conditions, it is shown that the washes result in the removal of significant amounts of seed proteins from the oil body preparation. These proteins include proteins which might be allergenic.

A total of 10–15 kgs of dry canola seed (*Brassica napus* cv Westar), maize (*Zea mays*) or sunflower (*Helianthus annuus*) was poured through the hopper of a colloid mill (Colloid Mill, MZ-130 (Fryma)), which was equipped with a MZ-120 crosswise toothed rotor/stator grinding set and top loading hopper. Approximately 50–75 l water was supplied through an externally connected hose prior to milling. Operation of the mill was at a gap setting of 1R, chosen to achieve a particle size less than 100 micron at 18° C. and 30° C. Following grinding of the seeds, tap water was added to the seed slurry to a final volume of 60–90 liters and a sample of the seed slurry was obtained for SDS gel electrophoresis. The slurry was then pumped into a decantation centrifuge (Hasco 200 2-phase decantation centrifuge maximum operating speed 6,000 rpm) after bringing the centrifuge up to an operating speed of 3,500 rpm. Transfer from the mill to the decantation centrifuge was achieved using a 1 inch M2 Wilden air operated double diaphragm pump. In 15–20 minutes approximately 15 kg of seed was decanted. A sample from the decanted liquid phase was obtained for SDS gel electrophoresis. Separation of the oil body fraction was achieved using a Sharples Tubular Bowl Centrifuge model AS-16 (Alpha Laval) equipped with a three phase separating bowl and removable ring dam series; capacity: 150 L/hr; ringdam: 29 mm. Operating speed was at 15,000 rpm (13,200×g). A Watson-Marlowe (Model 704) peristaltic pump was used to pump the decanted liquid phase into the tubular bowl centrifuge after bringing the centrifuge up to operating speed. The unwashed oil body phase was obtained and mixed with approximately 5 volumes of water. This procedure was repeated a total of three more times. The oil body phase which was obtained following the first spin, is referred to as an unwashed oil body preparation. All other preparations are washed oil body preparations. Samples for analysis by SDS gel electrophoresis were obtained following the first and fourth separations.

Upon completion of the fourth wash a 0.9 ml sample of the oil body preparation was homogenized in 0.1 ml 1 M $Na_2CO_3$ and left at room temperature for 30' with agitation. The washed oil body fraction was then recovered following centrifugation, washed once with water and prepared for SDS gel electrophoresis.

Figure 2:
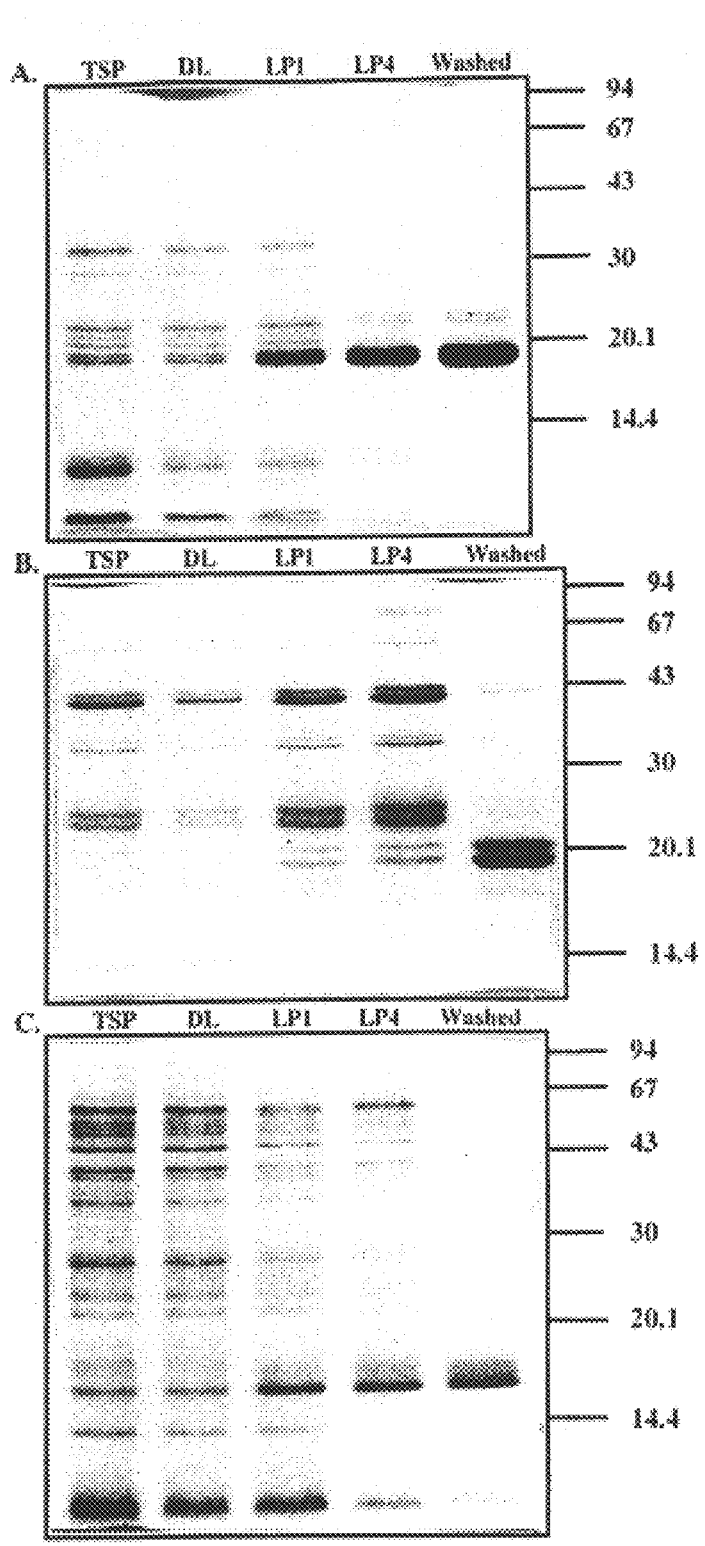
FIG. 2A–C are Coomassie blue stained gels showing the protein profiles of various seed fractions obtained from *Brassica napus* (Canola) (A), sunflower (B), and maize (C). The gels show the following fractions (1) total seed protein (TSP), (2) decanted liquid phase (DL), (3) unwashed oil bodies (LP1), (4) three washes with water (LP4), (5) four washes with water and one wash with 100 mM $Na_2CO_3$ (Washed).

All of the samples were dissolved in SDS sample buffer and the samples were analyzed by SDS gel electrophoresis. The results are shown in FIG. 2.

Example 4

The effect of washing the oil body phase on water retention characteristics. A washed oil body preparation and an unwashed oil body phase were prepared from rapeseed as in example 2. To determine the difference in water retention capacity between the unwashed oil body phase and the washed oil body preparation, 30 mls of oil body preparations were thoroughly mixed using a vortex. The preparations were then incubated for 2 hours in a water bath at 40, 60 or 80° C. and the samples were centrifuged at 1,500×g for 20 minutes (undiluted samples). Another set of samples was prepared by mixing 15 g of washed or unwashed oil body preparation with 15 ml of water. The samples were mixed on a vortex and then incubated at 40, 60 or 80° C. for 2 hours and the amount of water present in the samples was determined following centrifugation at 1,500×g for 20 minutes (diluted samples). Loss of mass attributable to evaporation was measured at 80° C. and 60° C.

At 80° C., the undiluted preparations comprising oil bodies lost significant amounts of water through evaporation. The preparation of unwashed oil bodies lost 26% of their mass, while the washed preparation lost 16%. Upon centrifugation the unwashed preparation released approximately 2.5 ml of aqueous phase, while the washed oil bodies remained in the same phase. Both diluted preparations absorbed water. The volume of oil bodies increased in both cases to 18.5±1 ml.

At 60° C., the undiluted preparations lost approximately 10% of water through evaporation. Following centrifugation, the washed preparation released about 0.5 ml of aqueous phase, while the washed oil body preparation stayed in the same phase. Both diluted preparations absorbed water. At 60° C., the volume of oil bodies increased in both cases to 18±1 ml.

At 40° C., the undiluted samples both released approximately 2 ml of aqueous phase. When the diluted samples were compared, the unwashed preparation absorbed about 3 ml of water, as was the case at 60 or 80° C. However the washed preparation absorbed 8 ml of water at 40° C.

These experiments demonstrate that in a washed oil body preparation heated to 60° C. or 80° C., water remains more tightly associated with the oil body preparation than in an unwashed preparation. When cooled down the washed oil body preparation appeared to be more stable than the unwashed emulsion. When heated to 40° C., the washed oil body preparation was able to absorb a larger volume of exogenously added water without resulting in phase separation offering greater flexibility in preparing oil body based formulations.

Example 5

The effect of washing oil bodies on oil absorption characteristics. A washed oil body preparation and an unwashed oil body phase were prepared from rapeseed as in example 2. To determine the difference in oil absorption capacity between the unwashed oil body phase and the washed oil body preparation, 2 gr of the oil body preparations was dispersed into 12 ml of refined, bleached, deodorized canola oil in a 50 ml tube. The contents were stirred for 30 seconds every 5 minutes for 30 min. The tubes were then centrifuged at 4,400 rpm for 25 min. The free oil was decanted and the percentage of absorbed oil was determined by weight difference. Three preparations of washed oil bodies were tested and three preparations of unwashed oil bodies were tested.

The oil absorption capacity of unwashed oil bodies was found to vary significantly between the three batches and varied from 18.7% to 28%. Washed oil bodies had reproducible oil absorption of 32±1%. Thus the washed oil body preparation was found to be superior since (1) a larger amount of oil was found to be absorbed and (2) the absorption occurred in a more reproducible manner.

Example 6

Preparation of a mayonnaise-like emulsion comprising a washed oil body preparation. A washed oil body preparation was prepared from rapeseed as in example 2 and a mayonnaise-like emulsion was produced by mixing the following components using a domestic electric blender.

| | |
|---|---|
| Sunflower oil | 78 gr |
| Egg yolk | 8 gr |
| Vinegar | 9 gr |
| Salt | 0.5 gr |
| Washed oil bodies | 5 gr |

A product with a mayonnaise-like texture was obtained. The mayonnaise-like product was stable for at least 1 day at 4° C.

Example 7

Preparation of a cholesterol-free mayonnaise-like emulsion. A washed oil body preparation was prepared from rapeseed as in Example 2 and a mayonnaise-like emulsion was produced by mixing the following ingredients:

| | |
|---|---|
| Sunflower oil | 200 gr |
| Washed oil bodies | 100 gr |
| Vinegar | 30 ml |

A product with a mayonnaise-like texture was obtained. Since the mayonnaise is prepared without egg yolk, an ingredient commonly employed in commercially obtainable mayonnaises, the product prepared using washed oil bodies is free of cholesterol. The mayonnaise was found to be as stable as a commercial mayonnaise when stability was assessed using centrifugation.

Example 8

Preparation of a vinaigrette-like emulsion comprising a washed oil body preparation. A washed oil body preparation was prepared from rapeseed as in example 2 and a vinaigrette-like emulsion was produced by manual mixing of the following components.

| | |
|---|---|
| Sunflower Oil | 17.5 gr |
| Mustard | 0.4 gr |
| Vinegar | 0.5 gr |
| Washed oil bodies | 7.7 gr |

A product with a vinaigrette-like texture was obtained. The vinaigrette-like product was stable for at least several days at 4° C.

Example 9

Preparation of a spreadable mustard-like product. A washed oil body preparation was obtained from rapeseed as outlined in example 2. The following ingredients were mixed to obtain a mustard-like product.

| | |
|---|---|
| Mustard | 70 gr |
| Washed oil bodies | 30 gr |

The resulting emulsion formulation is a mustard-like product which may easily be spread and has creamier, less gritty taste characteristics than mustard.

Example 10

Preparation of a bechamel-like sauce. A washed oil body preparation was obtained from rapeseed as outlined in example 2. The washed oil body preparation was heated at moderate heat and an equal part of flour was added and mixed with the heated washed oil body preparation. While stirring manually, milk was gradually added to this mixture.

| | |
|---|---|
| Flour | 50 gr |
| Washed Oil bodies | 50 gr |
| Milk | 100 ml–1 l. |

A bechamel-like sauce was obtained. The consistency of the sauce may be as desired depending on the amount of milk which is added. Additional flavorants also may be added as required. The absence of hydrogenated fatty acids in this product gives it an advantage over a sauce prepared from common domestic margarine.

Example 11

Preparation of a pharmaceutical emulsion for coating onto fish food. A washed oil body preparation from a transgenic *B. napus* plant which expresses carp growth hormone (cGH) fused to oleosin, wherein the fusion protein was targeted to the oil bodies, was obtained as follows. A DNA fragment containing the cGH coding region lacking its 22 amino acid signal sequence was amplified from a plasmid containing on an insert a common carp (*Cyprinus carpio*) growth hormone cDNA (Koren et al., 1989, Gene 67: 309–315) using the polymerase chain reaction in combination with two cGH specific primers. The amplified cGH fragment was fused in the correct reading frame and 3' to the *Arabidopsis thaliana* oleosin using pOThromb (van Rooijen, 1993, PhD Thesis, University of Calgary) as a parent plasmid and employing cloning strategies known to a person skilled in the art. In pOThromb a thrombin cleavage site was engineered 3' to the oleosin coding sequence. The oleosin-CGH fusion gene was introduced into the binary vector pCGN1559 (McBride and Summerfelt, 1990, Plant Mol. Biol. 14: 269–276) and the resulting construct was used to transform *A. tumefaciens*. The agrobacterium strain was employed to transform *B. napus* cv Westar seedlings. Seeds from transgenic plants were obtained and oil bodies were isolated from transgenic seed as outlined in example 1.

The oil bodies were subsequently taken up in a syringe and sprayed onto fish food using approximately 2.5 µg of oil body protein per 1 mg of fish food. The fish food coated with oil bodies was then left overnight to dry. A total of 50 mg of fish food was then mixed with 10 ml of water and was incubated for 0, 30, 45 or 60 minutes. The food was then collected and resuspended in 0.2 ml of 50 mM Tris-Cl (pH 7.5) and prepared for analysis by SDS gel electrophoresis upon boiling in 2.5% SDS. The presence of the oil bodies on the fish food was assessed using Western blotting and monoclonal antibodies against cGH.

Judging by the intensity of the signal of the single band observed in each lane on the Western blot, the oil bodies comprising cGH remained tightly associated with the fish food upon incubation of the oil bodies in water. Fish food which was incubated for 30, 45 or 60 minutes in water was shown to contain approximately the same amounts of cGH as the control fish food which was not incubated in water.

This example demonstrates that a transgenic plant variety can be prepared which imparts specific desirable properties to an emulsion. The example further demonstrates that an emulsion can be prepared from a washed oil body preparation which can be used as a coating or film. Finally, this example demonstrates that the washed oil body preparation may be employed to formulate a pharmaceutical composition.

Example 12

Preparation of base formulation emulsions comprising washed safflower oil bodies for use in a personal care product. A washed oil body preparation was prepared from safflower as in example 2. To the washed oil body preparation was added: 0.1% Glydant Plus, 0.1% Butylated Hydroxyanisole (BHA) 0.1% Butylated Hydroxytoluene (BHT) and a base formulation for use in a cosmetic product was prepared as follows. The oil bodies were transferred into a mixing pot and keltrol was added and was hydrated at room temperature with a high-speed propeller. Subsequently the glycerin was added. The mixture was then heated to 45–50° C., at 50° C. the BHA and BHT were added. Finally the Glydant Plus was added. The procedure for Base B and C was slightly different as the temperature was subsequently increased to 60° C. and the Arlacel 165 is added and mixed until the texture is homogeneous. The mixture was then cooled to 30° C. quickly with moderate propeller mixing.

| Base A | |
|---|---|
| Hydrated safflower oil bodies (0.1% Glydant Plus, 0.1% BHT, 0.1% BHA) | 96.95% |
| Glydant Plus | 0.15% |
| BHT | 0.1% |
| BHA | 0.1% |
| Keltrol | 0.7% |
| Glycerine | 2.0% |

-continued

| Base B | |
|---|---|
| Hydrated safflower oil bodies (0.1% Glydant Plus, 0.1% BHT, 0.1% BHA) | 94.45% |
| Glydant Plus | 0.15% |
| BHT | 0.1% |
| BHA | 0.1% |
| Keltrol | 0.7% |
| Glycerine | 2.0% |
| Arlacel | 2.5% |
| Base C | |
| Hydrated safflower oil bodies (0.1% Glydant Plus, 0.1% BHT, 0.1% BHA) | 94.75% |
| Glydant Plus | 0.25% |
| BHT | 0.1% |
| BHA | 0.1% |
| Keltrol | 0.7% |
| Glycerine | 2.0% |
| Arlacel | 2.5% |

The hydrated safflower oil body preparation alone and all three bases were shown to be stable with respect to oxidation and microbial growth. Similarly, little or no change was observed in either the colour or odor of these three base formulations.

The chemical analysis of the hydrated safflower oil body preparation revealed that the sample contained 50.82% water and 49.18% dry weight. The dry weight (DW) component consisted of 3.76% protein, 93.56% oil and 2.68% other.

Example 13

Preparation of base formulation emulsions for use in a cosmetically elegant product. Base B was further modified for use in cosmetically elegant topical formulations. The formulation was mixed to an emulsion with the following procedure. Phase I is the water phase. In this phase, the water in the main tank is charged. A propeller is used to hydrate the keltrol, panthenol and allantoin with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75 to 77° C. The oil phase ingredients include, Dimethicone 350, Cetyl Alcohol, Arlacel 165, Finsolv TN, Sesame Oil, Vitamin E Acetate, and Phenonip. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At approximately 40° C. Base Formulation B is added slowly. The mixture is allowed to cool to room temperature.

| Keltrol | 0.5% |
|---|---|
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |

-continued

| Sesame Oil | 1.0% |
|---|---|
| Vitamin E Acetate | 0.05% |
| Phenonip | 1.0% |
| Base Formulation B | 10.0% |
| Water | 77.8% |

Example 14

Preparation of base formulation emulsions for use in a cosmetically elegant product. Base C was further modified for use in cosmetically elegant topical formulations. The formulation was mixed to an emulsion with the following procedure. Phase I is the water phase. In this phase, the water in the main tank is charged. A propeller is used to hydrate the keltrol, panthenol and allantoin with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75° C. to 77° C. The oil phase ingredients include, Dimethicone 350, Cetyl Alcohol, Arlacel 165, Finsolv TN, Isohexadecane, Vitamin E Acetate, and Phenonip. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At approximately 40° C. Base Formulation C are added slowly. The mixture is allowed to cool to room temperature.

| Keltrol | 0.5% |
|---|---|
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Isohexadecane | 2.0% |
| Vitamin E Acetate | 0.05% |
| Phenonip | 1.0% |
| Base Formulation C | 20.0% |
| Water | 66.8% |

Example 15

Preparation of base formulation emulsions for use in a cosmetically elegant product. Base B was further modified for use in cosmetically elegant topical formulations. The formulation was mixed to an emulsion with the following procedure. Phase one is the water phase. In this phase, the water in the main tank is charged. A propeller is used to hydrate the keltrol, panthenol and allantoin with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75° C. to 77° C. The oil phase ingredients include, SEE 839, Cetyl Alcohol, Arlacel 165, Finsolv TN, Vitamin E Acetate, and Phenonip. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At approximately 40° C. Base Formulation B are added slowly. The mixture is allowed to cool to room temperature.

| Keltrol | 0.5% |
| --- | --- |
| Panthenol | 0.1% |
| Allantoin | 0.05% |
| Glycerin | 2.0% |
| SEE 839 | 1.0% |
| Arlacel 165 | 2.5% |
| Cetyl Alcohol | 2.0% |
| Finsolv TN | 2.0% |
| Vitamin E Acetate | 0.05% |
| Phenonip | 1.0% |
| Base Formulation B | 40.0% |
| Water | 48.8% |

Example 16

Preparation of a sunscreen with a sun protection factor of 8. Bases B was further modified for use in cosmetically elegant sunscreen. The formulation was mixed to an emulsion with the following procedure. Phase I is the water phase. In this phase, the water in the main tank is charged. A propeller is used to hydrate the keltrol, panthenol and allantoin with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75° C. to 77° C. The oil phase ingredients include, Dimethicone, Cetyl Alcohol, Arlacel 165, Finsolv TN, Sesame Oil, Vitamin E Acetate, and Phenonip. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At approximately 40° C. Base Formulation B are added slowly. The mixture is allowed to cool to room temperature.

| Keltrol | 0.5% |
| --- | --- |
| Panthenol | 0.1% |
| Allantoin | 0.05% |
| Glycerin | 2.0% |
| Dimethicone | 1.0% |
| Arlacel 165 | 2.5% |
| Cetyl Alcohol | 2.0% |
| Finsolv TN | 2.0% |
| Sesame Oil | 1.0% |
| Vitamin E Acetate | 0.05% |
| Phenonip | 1.0% |
| Base Formulation B | 10.0% |
| Water | 77.8% |

Example 17

Preparation of a sunscreen with a sun protection factor of 8. The formulation was mixed to an emulsion with the following procedure. Phase I is the water phase. In this phase, the water in the main tank is charged. A propeller is used to hydrate the Kaolin and the Veegum Ultra with moderate agitation at room temperature. The glycerin is then added with continued mixing. The water phase is heated to a final temperature of 75° C. to 77° C. and methylparaben is added. Phase II, the oil phase is mixed in a separate mixing pot with moderate agitation and then subsequently heated up to 75° C. to 77° C. The oil phase ingredients include, Dimethicone 250, Cetyl Alcohol, Arlacel 165, Propylparaben, Safflower Oil, Trivalin SF, Palemol OL and Parsol MCX. The final step of emulsification includes the addition of the oil phase Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At 40° C. the Germall 115 is added and when the temperature reaches about 37° C. to 40° C. the safflower oil bodies are added slowly. The mixture is allowed to cool to room temperature and the color (red 33 solution) is added. The final pH was 6.0 and viscosity was 25,000 cps.

| Purified Water | 47.15% |
| --- | --- |
| Kaolin USP | 2.50% |
| Veegum Ultra (Mg, Al Sillicate) | 5.00% |
| Glycerin | 2.00% |
| Methylparaben | 0.30% |
| Dimethicone 350 | 0.50% |
| Cetyl Alcohol | 2.00% |
| Arlacel 165 (Glyceryl Stearate & PEG-100 Stearate) | 2.50% |
| Propylparaben | 0.15% |
| Safflower Oil | 2.00% |
| Trivalin SF (Ethyoxydiglycol) | 2.00% |
| Palemol OL (Oleyl Lactate) | 1.00% |
| Parsol MCX (Octyl Methoxycinnamate) | 7.50% |
| Germall 115 (Imidazolidinyl Urea) | 0.30% |
| Hydrated Safflower Oil Body (0.1% Glydant Plus, 0.1% BHT, 0.1% BHA) | 25.00% |
| Red #33 1% | 0.10% |

Example 18

Preparation of a skin care cream containing a stable vitamin A derivative, retinyl palmitate. Base C was further modified for use in cosmetically elegant skin care cream containing a stable vitamin A derivative, retinyl palmitate. The formulation was mixed to an emulsion with the following procedure. Phase I is the water phase. In this phase, the water in the main tank is charged. A propeller is used to hydrate the Keltrol, Panthenol and Allantoin with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75° C. to 77° C. The oil phase ingredients include Dimethicone 350, Cetyl Alcohol, Arlacel 165, Finsolv TN, Permethyl 101A, Phenonip and Petinyl Palmitate. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At 40° C. the Base Formulation C is added slowly.

| Keltrol | 0.5% |
| --- | --- |
| Panthenol | 0.1% |
| Allantoin | 0.05% |
| Glycerin | 2.0% |
| Dimethicone | 1.0% |

| | |
|---|---|
| Arlacel 165 | 2.5% |
| Cetyl Alcohol | 2.0% |
| Finsolv TN | 2.0% |
| Permethyl 101A | 2.0% |
| Phenonip | 1.0% |
| Base Formulation C | 50.0% |
| Water | 35.85% |
| Retinyl Palmitate | 1.0% |

Example 19

Preparation of a day cream. The formulation was mixed to an emulsion with the following procedure. Phase I is the water phase. In this phase, the water in the main tank is charged. A propeller is used to hydrate the Kaolin and the Mg, Al Silicate with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75° C. to 77° C. The oil phase ingredients include, Dimethicone 350, Cetyl Alcohol, Arlacel 165, Trivalin SF, and Palemol OL. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At 40° C. the Germaben II is added and when the temperature reaches about 37° C. to 40° C. the safflower oil bodies are added slowly. The mixture is allowed to cool to room temperature. The final pH was adjusted to 6.00 with a final viscosity of 25,060 cps.

| | |
|---|---|
| Purified water | 32.20% |
| Kaolin | 2.50% |
| Veegum Ultra (Mg, Al Silicate) | 5.00% |
| Glycerin | 2.00% |
| Dimethicone 350 | 0.50% |
| Cetyl Alcohol | 2.00% |
| Arlacel 165 (Glyceryl Sterate & PEG-100 Stearate) | 2.50% |
| Trivalin SF (Ethoxydiglycol) | 2.00% |
| Palemol OL (Oleyl Lactate) | 1.00% |
| Germaben II (Diazolidinyl Urea) | 0.30% |
| Hydrated Safflower Oil Body (0.1% Glydant Plus, 0.1% BHT, 0.1% BHA) | 50.00% |

Example 20

Preparation of a night cream. The formulation was mixed to an emulsion with the following procedure. Phase I is the water phase. In this phase, the water in the main tank is charged. A propeller is used to hydrate the Kaolin and the Mg, Al Silicate with moderate agitation at room temperature. The glycerin is then added with continued mixing. The water phase is heated to a final temperature of 75° C. to 77° C. Phase II, the oil phase is mixed in a separate mixing pot with moderate agitation and then subsequently heated up to 75° C. to 77° C. The oil phase ingredients include, Dimethicone 350, Cetyl Alcohol, Arlacel 165, Trivalin SF, Palemol OL. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 60° C. The agitation is decreased as the temperature decreases. At 60° C. Glycolic acid is added, at 50° C. a 25% solultion of sodium hydroxide is added, at 40° C. the Germall 115 is added and when the temperature reaches about 37 to 40° C. the safflower oil bodies are added slowly. The final pH was adjusted to 3.64 with a final viscosity of 35,000 cps.

| | |
|---|---|
| Purified water | 24.20% |
| Kaolin | 2.50% |
| Veegum Ultra (Mg, Al Silicate) | 5.00% |
| Glycerin | 2.00% |
| Dimethicone 350 | 0.50% |
| Cetyl Alcohol | 2.00% |
| Arlacel 165 (Glyceryl Sterate & PEG-100 Stearate) | 2.50% |
| Trivalin SF Ethoxydiglycol) | 2.00% |
| Palemol OL (Oleyl Lactate) | 1.00% |
| Glycolic Acid | 8.00% |
| Sodium Hydroxide (25% solution) | qs pH 3.3–3.8 |
| Germaben II (Diazolidinyl Urea) | 0.30% |
| Hydrated Safflower Oil Body (0.1% Glydant Plus, 0.1% BHT, 0.1% BHA) | 50.00% |

Example 21

Preparation of a facial mask. The formulation was mixed to an emulsion with the following procedure. Phase I is the water phase. In this phase, the water in the main tank is charged. A propeller is used to hydrate the Kaolin and the Mg, Al Silicate with moderate agitation at room temperature. The glycerin is then added with continued mixing. The water phase is heated to a final temperature of 75° C. to 77° C. and methylparaben, Green Clay and Bentonite NF BC are added. Phase II, the oil phase is mixed in a separate mixing pot with moderate agitation and then subsequently heated up to 75° C. to 77° C. The oil phase ingredients include, Dimethicone 350, Trivent OC-G, Arlacel 165, Polyparabin and Safflower Oil. The final step of emulsification includes the addition of the oil phase (Phase II) to the water phase (Phase I). The two phases are mixed under high agitation with a propeller or homogenizer for 15 minutes. After 15 minutes of mixing the mixture is cooled slowly to 40° C. The agitation is decreased as the temperature decreases. At 40° C. the Germall 115 and Phytic acid is added and when the temperature reaches about 37° C. to 40° C. the safflower oil bodies are added slowly. The final pH was 1.49 and viscosity is 45,000 cps.

| | |
|---|---|
| Distilled Water | 44.25% |
| Kaolin | 2.50% |
| Glycerin | 2.00% |
| Methylparaben | 0.30% |
| Green Clay (Montmorillonate) | 0.30% |
| Bentonite NF BC | 10.00% |
| Dimethicone 350 | 0.50% |
| Trivent OC-G (Tricaprylin) | 2.00% |
| Glyceryl Stearate & PEG-100 Stearate | 2.00% |
| Propylparabin | 0.15% |
| Safflower oil | 1.00% |
| Germall 115 (Imidazolidinyl Urea) | 0.30% |
| Hydrated Safflower oil body (0.1% Glydant Plus, 0.1% BHT, 0.1% BHA) | 25.00% |
| Phytic Acid | 5.00% |

Example 22

Comparison of Washed Oil Bodies and Lipid Vesicles in the Preparation of Cosmetic Formulations. Washed Oil bodies were prepared as described in example 2, pasteurized and 0.1% BHT, 0.1% BHA and 0.1% Glydant plus added. Lipid vesicles were prepared in accordance with the specification of U.S. Pat. No. 5,683,740 except that they were prepared from safflower seed, pasteurized and 0.1% BHT, 0.1% BHA and 0.1% Glydant Plus was added.

The oil bodies and lipid vesicles were compared with respect to emulsion stability, color changes, odor changes, viscosity, microbial growth and cosmetic desirability parameters. To evaluate stability, the samples were tested at 45° C., 4° C. and room temperature (3 months at 45° C. is equivalent to approximately 2 year shelf life at room temperature). To evaluate emulsion stability, 150 g of each sample was maintained at 45° C., 75 g of each sample was maintained at room temperature or at 4° C. Emulsion stability was evaluated for emulsion separation, oil droplet separation and coalescence. The 4° C. sample was used as the reference for comparison. Color changes were evaluated by visual inspection. Color was evaluated on the accelerated oven sample (45° C.) and the room temperature sample and compared to the 4° C. as a reference. Odor was tested as with the color with the 4° C. sample used as a reference point. In order to maintain consistency, the odor was judged by two individuals who both agreed on the evaluation. Viscosity of each sample was measured at room temperature using a RVT Model viscometer with Spindle E at 10 rpm. Microbial growth was measured on 10 g of each sample. The sample was diluted and 1 ml of the sample is added to 49° C. Tryptic Soy Agar, swirled and allowed to cool. The plates were incubated at 35° C. for 48 hours and a colony count was taken. Finally, cosmetic attributes were evaluated by 3 individuals, 2 individuals who were familiar with oil bodies/ lipid vesicles and 1 person who was not. Cosmetic attributes include skin penetration, residue left on the skin after the sample was rubbed in, dryness (lack of moisture) and oiliness.

Table 1 summarizes the results for the oil bodies. The pH for the oil body sample was constant at 6.50 throughout the test at room temperature and at 45° C. The oil body preparation, when applied to the skin, distributed evenly on the skin, was fast penetrating and left almost no residue on the skin surface. The oil body preparation was also stable with respect to color, odor, viscosity and emulsion stability.

Table 2 summarizes the results for the lipid vesicles. The pH for the lipid vesicle sample is difficult to measure because of the total separation but was approximately 6.8. The lipid vesicle preparation, when applied to the skin, was very oily and left a film residue on the skin. The lipid vesicle preparation was stable with respect to microbial growth but was not stable with respect to color, odor and emulsion stability.

The above results demonstrate that the oil washed oil body preparation is clearly superior to lipid vesicles with respect to both physical parameters (color, odor, stability) and cosmetic parameters (penetration, residual residue, and oiliness). These parameters are critical to the preparation of personal care products.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

| Time (days) | Color | Odor | Stability | Viscosity (cps) | Microbial Growth |
|---|---|---|---|---|---|
| Room Temperature | | | | | |
| 0 | Pale yellow | Very Mild | No separation | 3500 +/− 100 | 500 |
| 14 | Pale yellow | No change | No separation | 3500 +/− 100 | 300 |
| 25 | Pale yellow | No change | No separation | 3500 +/− 100 | <10 |
| 45° C. | | | | | |
| 0 | Pale yellow | Very Mild | No separation | 3500 +/− 100 | 500 |
| 14 | Pale yellow | Mild | No separation | 4000 +/− 100 | <20 |
| 25 | Mildly yellow | Mild | No separation | 4000 +/− 100 | <10 |
| 4° C. | | | | | |
| 0 | Pale yellow | Very Mild | No separation | 3500 +/− 100 | 500 |
| 14 | Pale yellow | Very Mild | No separation | 3500 +/− 100 | 250 |
| 25 | Pale yellow | Very Mild | No separation | 3500 +/− 100 | <10 |

TABLE 2

| Time (days) | Color | Odor | Stability | Viscosity (cps) | Microbial Growth |
|---|---|---|---|---|---|
| Room Temperature | | | | | |
| 0 | Dark yellow | Very Mild | Separation | Approx. 4000 | <20 |
| 14 | Dark yellow | Very Mild | Total Separation | Sluggish | <20 |
| 25 | Darker yellow | Very Mild | Total Separation | Sluggish | <10 |
| 45° C. | | | | | |
| 0 | Dark yellow | Neutral | No separation | 3500 +/− 100 | <20 |
| 14 | Brown | Amine Odor | No separation | 4000 +/− 100 | <10 |
| 25 | Dark brown | Fishy | No separation | 4000 +/− 100 | <10 |
| 4° C. | | | | | |
| 0 | Dark yellow | Neutral | Separation | Approx. 4000 | <20 |
| 14 | Dark yellow | Neutral | No separation | 3500 +/− 100 | <10 |
| 25 | Dark yellow | Neutral | No separation | 3500 +/− 100 | <10 |

We claim:

1. A method for preparing an emulsion formulation comprising:
  (1) obtaining oil bodies from plant seeds by a method that comprises:
    (a) grinding plant seeds to obtain ground seeds comprising substantially intact oil bodies;
    (b) removing solids from the ground seeds; and
    (c) separating the oil body phase from the aqueous phase;
  (2) washing the oil body phase to yield a washed oil body preparation; and (3) formulating the washed oil body preparation into an emulsion for use in the preparation of a personal care product.

2. A method according to claim 1 wherein said washed oil body preparation comprises less than about 75% (w/w) of the endogenously present non-oil body seed proteins.

3. A method according to claim 1 wherein said washed oil body preparation comprises less than about 50% (w/w) of the endogenously present non-oil body seed proteins.

4. A method according to claim 1 wherein said washed oil body preparation comprises less than about 10% (w/w) of the endogenously present non-oil body seed proteins.

5. A method according to claim 1 wherein said grinding results in the release of less than about 50% (v/v) of the total seed oil content in the form of free oil.

6. A method according to claim 1 wherein said grinding results in the release of less than about 20% (v/v) of the total seed oil content in the form of free oil.

7. A method according to claim 1 wherein said grinding results in the release of less than about 10% (v/v) of the total seed oil content in the form of free oil.

8. A method according to claim 1 wherein a liquid phase is added prior to or during the grinding step.

9. A method according to claim 8 wherein a liquid phase is added to the washed oil bodies and the liquid phase and washed oil bodies are mixed until an emulsion is formed.

10. A method according to claim 8 wherein said liquid phase is water.

11. A method according to claim 9 wherein said liquid phase is present in the emulsion in an amount varying from about 1% to about 99% v/v.

12. A method according to claim 1 wherein said plant seed is obtained from the group of plants consisting of rapeseed (Brassica spp.), soybean (*Glycine max*), sunflower (*Helianthus annuus*), oil palm (*Elaeis guineeis*), cottonseed (Gossypium spp.), groundnut (*Arachis hypogaea*), coconut (*Cocus nucifera*), castor (*Ricinus communis*), safflower (*Carthamus tinctorius*), mustard (Brassica spp. and *Sinapis alba*), coriander (*Coriandrum sativum*), squash (*Cucurbita maxima*), linseed/flax (*Linum usitatissimum*), Brazil nut (*Bertholletia excelsa*) jojoba (*Simmondsia chinensis*) and maize (*Zea mays*).

13. A method according to claim 1 wherein said solids are removed by centrifugation or filtration of said ground seeds.

14. A method according to claim 1 wherein said oil body phase is separated from said aqueous phase by a gravity based method or a size exclusion based method.

15. A method according to claim 1 in which said formulating comprises the addition of a preservative agent, an anti-oxidant or an emulsion stabilizing agent.

16. A method according a claim 1 in which the seed is immersed in a liquid phase prior to grinding for from approximately 15 minutes to approximately 2 days.

17. An emulsion comprising a washed oil body preparation comprising substantially intact oil bodies.

18. An emulsion according to claim 17 further comprising a liquid phase.

19. An emulsion according to claim 18 wherein said liquid phase is water.

20. An emulsion according to claim 19 further comprising a preservative, an anti-oxidant or an emulsion stabilizer.

21. An emulsion according to claim 17 wherein the oil bodies are obtained from a plant.

22. An emulsion according to claim 17 wherein the oil bodies are obtained from a plant selected from the group consisting of rapeseed (Brassica spp.), soybean (*Glycine max*), sunflower (*Helianthus annuus*), oil palm (*Elaeis guineeis*), cottonseed (Gossypium spp.), groundnut (*Arachis hypogaea*), coconut (*Cocus nucifera*), castor (*Ricinus communis*), safflower (*Carthamus tinctorius*), mustard (Brassica spp. and *Sinapis alba*), coriander, (*Coriandrum sativum*), squash (*Cucurbita maxima*), linseed/flax (*Linum usitatissimum*), Brazil nut (*Bertholletia excelsa*) jojoba (*Simmondsia chinensis*) and maize (*Zea mays*).

23. A personal care product comprising an emulsion prepared according to the method of claim 1.

* * * * *